United States Patent [19]

Howard et al.

[11] 4,104,365
[45] Aug. 1, 1978

[54] METHOD OF SEPARATING SULFURIC ACID FROM NEUTRAL SODIUM SULFATE IN SPENT CHLORINE DIOXIDE GENERATOR LIQUOR

[76] Inventors: John Howard, 5788 Olympic St., Vancouver, British Columbia; Derek Gordon Lobley, 18775-54th Ave., R.R. 3, Surrey, British Columbia, both of Canada

[21] Appl. No.: 794,740

[22] Filed: May 9, 1977

Related U.S. Application Data

[63] Continuation-in-part of Ser. No. 690,373, May 27, 1976, abandoned.

[51] Int. Cl.² ............... C01B 17/90; C01D 15/06
[52] U.S. Cl. .................... 423/531; 23/300; 423/199; 423/478; 423/551
[58] Field of Search ................ 423/527, 423/530, 531, 551, 478, 480, 199; 23/300, 302 R

[56] References Cited

U.S. PATENT DOCUMENTS

| | | | |
|---|---|---|---|
| 873,070 | 12/1907 | Nibelius | 23/302 |
| 2,482,830 | 9/1949 | Allen, Jr. | 23/302 |
| 3,331,661 | 7/1967 | Boiston et al. | 423/551 |
| 3,364,202 | 1/1968 | De Rooij et al. | 423/531 |
| 3,597,168 | 8/1971 | Hoppe et al. | 23/300 |
| 3,760,065 | 9/1973 | Rapson | 423/478 |
| 3,928,535 | 12/1975 | Schulz | 423/551 |
| 3,980,751 | 9/1976 | Foulkes | 423/478 |

FOREIGN PATENT DOCUMENTS

| | | | |
|---|---|---|---|
| 816,290 | 7/1959 | United Kingdom | 423/531 |
| 1,102,463 | 2/1968 | United Kingdom | 423/531 |

*Primary Examiner*—O. R. Vertiz
*Assistant Examiner*—Gary P. Straub
*Attorney, Agent, or Firm*—Fulwider, Patton, Rieber, Lee & Utecht

[57] ABSTRACT

A method of separating sulfuric acid from spent chlorine dioxide generator liquor. The method comprises simultaneously adding to the spent liquor, a water-soluble organic compound selected from the group consisting of alcohols and ketones, and water. The resulting solid is separated to leave an aqueous solution of sulfuric acid. The method is of particular application in acid and salt cake recovery from the effluent of a chlorine dioxide generator operating at an acid normality of between 6 and 11.

5 Claims, 2 Drawing Figures

METHOD OF SEPARATING SULFURIC ACID FROM NEUTRAL SODIUM SULFATE IN SPENT CHLORINE DIOXIDE GENERATOR LIQUOR

RELATED APPLICATION

This application is a continuation in part of application Ser. No. 690,373, filed May 27, 1976, and now abandoned.

FIELD OF THE INVENTION

This invention relates to a process for the recovery and recycle of sulfuric acid, and the separation and disposal of sodium sulfate from the spent liquor of a chlorine dioxide generator. This spent liquor of all $ClO_2$ generation processes contains sulfuric acid, sodium sulfate and water, with dissolved gases of chlorine dioxide and chlorine. In many instances of testing, high levels of chromium and relatively minor amounts of ferric, calcium and potassium cations were discovered in the spent solutions, as well as chloride and chlorate anions.

DESCRIPTION OF PRIOR ART

Chlorine dioxide is much used in the bleaching of pulp in paper making. The chlorine dioxide is produced by three principal processes, the Mathieson, Solvay and R-2 Processes. All these processes are essentially the reduction of a chlorate, usually sodium chlorate, in a strong sulfuric acid medium. Generally speaking, the processes differ in the reducing agent used. In the Mathieson Process and reducing agent is sulfur dioxide, in the Solvay Process the reducing agent is methanol and in the R-2 Process the reducing agent is the chloride ion.

The processes all operate at low chlorate, chloride and high acid concentration. The chlorine dioxide is removed from the reaction solution as a 10% gaseous mixture in air. The three reactions may be described by the following simplified equations:

Mathieson Process:

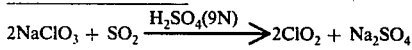
$$2NaClO_3 + SO_2 \xrightarrow{H_2SO_4(9N)} 2ClO_2 + Na_2SO_4$$

Solvay Process:

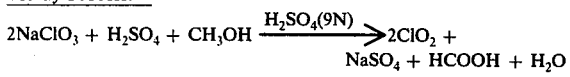
$$2NaClO_3 + H_2SO_4 + CH_3OH \xrightarrow{H_2SO_4(9N)} 2ClO_2 + NaSO_4 + HCOOH + H_2O$$

R-2 Process:

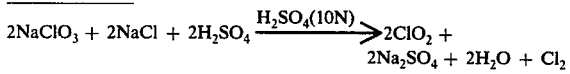
$$2NaClO_3 + 2NaCl + 2H_2SO_4 \xrightarrow{H_2SO_4(10N)} 2ClO_2 + 2Na_2SO_4 + 2H_2O + Cl_2$$

All the above processes require a continuous supply of sulfuric acid to maintain the 6–11N levels of acidity for efficient chlorine dioxide production. It should be noted that the Mathieson Process does not consume any acid, since sulfuric acid sufficient to combine with sodium added as chlorate is generated from the sulfur dioxide used as the reducing agent. Thus the Mathieson Process offers an excellent possibility of generating chlorine dioxide without the purchase of fresh acid provided that the acid in the effluent can be separated from the sodium salts and recycled. In the Solvay and R-2 Processes, recovery of acid from the effluent requires only the purchase of acid sufficient to convert sodium chlorate and chloride into sodium sulfate. An effective recovery process would ensure that there would be sufficient acid to maintain a generator acid levels of 6–11N.

The desirability of separating sulfuric acid from sodium sulfate in $ClO_2$ generator spent solutions is primarily necessitated by the need to control sulfidities in pulp mill cooking liquors. The current practice necessitates the incineration of these solutions, which creates the problem of sulfidity control. It was from this need that the SVP or R3 Systems were invented (U.S. Pat. No. 3,446,584), wherein a chlorine dioxide generator could operate at low normalities in order to separate the neutral salt and sulfuric acid. Both of these processes require the complete scrapping of existing generation equipment, whereas the present invention necessitates only the addition of equipment to an existing process without disruption of chemical production.

Effluents from chlorine dioxide generators have weight compositions in the range:
20 to 30% sodium sulfate; 25 to 35% sulfuric acid; balance water, dissolved $ClO_2$, $Cl_2$, $SO_2$, chrome, ferric, calcium chloride, and chlorate ions.

For example, a typical effluent from a Mathieson or Solvay Process would have the composition:

| | | |
|---|---|---|
| Sodium sulfate ($Na_2SO_4$) | 24.5% | w/w |
| Sulfuric acid ($H_2SO_4$) | 28.2% | w/w |
| Water | 46.3% | w/w |
| Sodium chlorate ($NaClO_3$) | 0.6% | w/w |
| Sodium chloride (NaCl) | 0.1% | w/w |
| Gases, etc. | 0.1% | w/w |

A typical effluent generated in the R-2 Process has the following approximate composition:

| | | |
|---|---|---|
| Sodium sulfate ($Na_2SO_4$) | 22.3% | w/w |
| Sulfuric acid ($H_2SO_4$) | 33.6 | w/w |
| Water | 44.0% | w/w |
| Sodium chlorate ($NaClO_3$) | 0.33% | w/w |
| Sodium chloride (NaCl) | 0.20% | w/w |
| Gases, etc. | 0.10% | w/w |

If one examines a phase diagram of the system $Na_2SO_4$—$H_2O$—$H_2SO_4$, it becomes clear that it is difficult to isolate sodium sulfate from the mixture. It will, of course, be realized that reference to the phase diagram is a simplification, as the effluent from the chlorine dioxide generator also contains chlorate, chloride, traces of chlorine dioxide, chlorine and various other chemicals. However, generally the effluents all lie in that area of the phase diagram where sodium bisulfate monohydrate ($NaHSO_4 \cdot H_2O$) crystallizes if the effluents are simply cooled. Crystallizing the bisulfate would offer some recovery of acid from the mother liquor but it is less than ideal as this salt carries with it 35.5% of its own weight of sulfuric acid. Thus, isolation of this salt from the R-2 Process effluent would remove as much as 46% of the total acid in the system. Isolation of the salt from the Mathieson Process effluent would represent a loss as high as 60%. Because of this difficulty, most previous acid recovery systems have attempted to solve the problem by the addition of water at some stage of the operation, to move from the bisulfate monohydrate to the neutral anhydrous or hydrated salt zones ($Na_2SO_4$ or its decahydrate) of the phase diagram. However, dilution with water usually requires either excessive cooling of the effluent — which is strong in sulfuric acid — or addition of sodium ions as chlorate in order to precipitate the neutral salt and leave the acid in the mother liquor for reuse. This, generally, is the basis of previous recovery systems reported in the literature. They have either necessitated complete abandonment of existing process equipment by building an R 3/SVP Process Plant, or they have required radical alteration of operating conditions to counterbalance the adverse effect of water on the generator efficiency; for example, the Low Acid Process (LAP) developed at Pittsburgh Plate Glass Industries Ltd.

The ability of pure anhydrous ethanol to decompose or split anhydrous sodium bisulfate into an intermediate acid sulfate having a formula $(Na_2SO_4)_3 H_2SO_4$, which may be considered equivalent to $Na_3H(SO_4)_2$, sodium sesquisulfate or tri-sodium hydrogen disulfate, was reported over 50 years ago by Dunnicliff and Butler, J. Chem. Soc. 117, 649 (1920). The reaction may be expressed as follows:

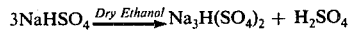

$$3NaHSO_4 \xrightarrow{Dry\ Ethanol} Na_3H(SO_4)_2 + H_2SO_4$$

Nibelius (U.S. Pat. No. 873,070), Allen (U.S. Pat. No. 2,482,830) and Boiston (U.S. Pat. No. 3,331,661) refer to the precipitation of Glauber's salts $(Na_2SO_4 10H_2O)$ and production of anhydrous sodium sulfate, by the action of, for example, alcohols on sulfuric acid-solution sulfate systems but it must be emphasized that the acidity levels in those systems are generally below 4N and other impurities are not present.

SUMMARY OF THE INVENTION

In examining the above reaction between sodium bisulfate and ethanol, reported by Dunnicliff and Butler, the present inventors have observed that if 5 to 50% of water, based on the volume of the organic compound, was added to the system then several other changes ocurred. These changes are:

1. The $NaHSO_4 H_2O$ could be completely split into neutral $Na_2SO_4$, not an intermediate sulfate which contained $H_2SO_4$.
2. The rate of splitting was increased.
3. Little, if any, sulfation of the alcohol by the liberated $H_2SO_4$ occurred.
4. Complete splitting occurred when only minor amounts of water were present in the system (thus bringing the normality of the sulfuric acid up to 4N). When the concentration was higher than this, splitting was usually halted at the $Na_3H(SO_4)_2$ stage.
5. Sodium sulfate remains unchanged in a system of aqueous alcohol containing less than 4N $H_2SO_4$ after several days, indicating that neutral sodium sulfate is a preferred product in aqueous alcohol containing less than 4N $H_2SO_4$.
6. The above changes also occur when the ethanol is replaced by other water-soluble organic solvents, in particular other alcohols and ketones. The alcohols include methanol, n-propanol and iso-propanol. The ketones include acetone. Methanol is a particularly preferred solvent because of its cheapness.

The invention thus relates to the separating of sulfuric acid and sodium sulfate from the effluent of a chlorine dioxide generator, which has a 6-11N level of acidity, the recycle of sulfuric acid back to the generator feed and the essential elimination of foreign materials, which prevent splitting of the acid from the neutral salt.

Accordingly, the present invention is a method of separating sulfuric acid and anhydrous sodium sulfate from the effluent of a chlorine dioxide generator having a normality with respect to sulfuric acid in the range of from 6 to 11, said effluent comprising sulfuric acid, sodium sulfate, water, dissolved gases and, possibly cations the method comprising:

oxidizing the residual chlorate in the effluent to chlorine dioxide and venting the chlorine dioxide;

purging dissolved gases from the effluent;

adding to the resulting, purged effluent a mixture of an organic compound selected from alcohols and ketones with 5 to 50% by volume, based on the volume of the organic compound, of water to precipitate anhydrous sodium sulfate from the effluent;

separating the anhydrous sodium sulfate;

passing the mother liquor from the sulfate separation to a distillation column;

separating the organic compound from the distillate by distillation; and recovering sulfuric acid from the still bottoms.

This acid/salt separation technology of the present invention is applicable to all present processes as well as new systems of chlorine dioxide generators, and permits cleaner and more effluent-free facilities, wherein all the mercaptans and sulfide values can be collected and used within the cooking liquor circuit by virtue of this sulfuric acid separation and recycling process.

Aspects of the invention are illustrated in the drawings in which.

Figure 1:
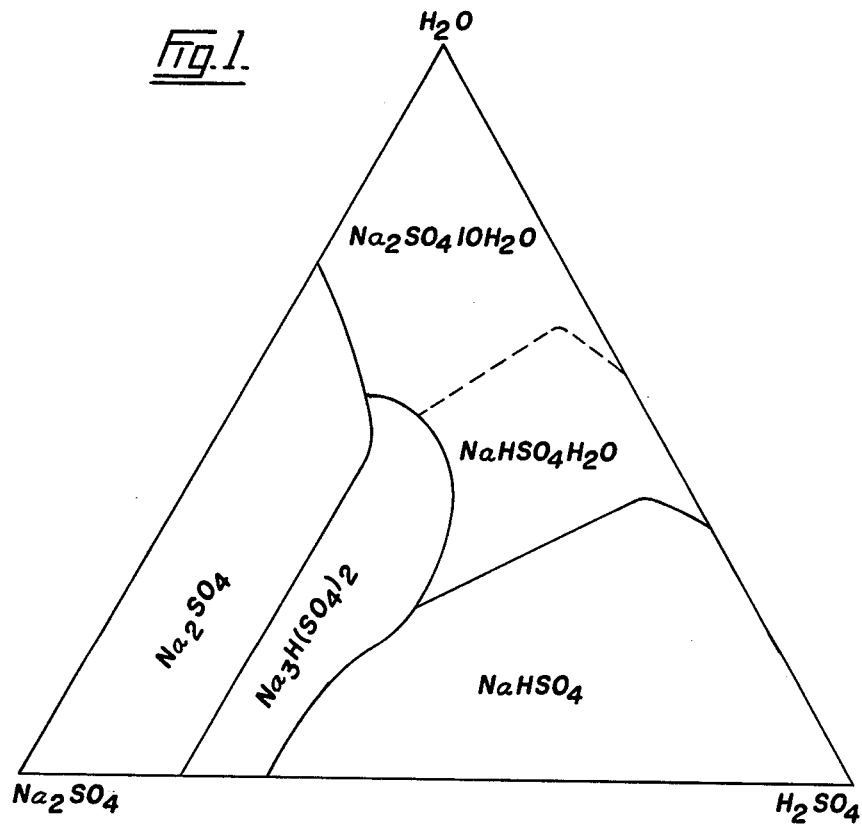
FIG. 1 is a phase diagram of the system sulfuric acid-sodium sulfate-water.

The $H_2SO_4$ — $Na_2SO_4$ — $H_2O$ proportions in the above effluents are such that these solutions fall into the general area of the phase diagram shown in FIG. 1 wherein $NaHSO_4 H_2O$ will precipitate upon cooling to below 20° C — see below.

The particular route and chemical mechanism invented takes the sodium bisulfate monohydrate through the sesquisulfate stage to the neutral salt. It should be noted that:

1. The mere addition of alcohol in any amount will not completely split $NaHSO_4$ to the neutral $Na_2SO_4$, but only to $Na_3H(SO_4)_2$, which contains 18.7% $H_2SO_4$. Only a specific amount of water will complete the split to the neutral salt.
2. Addition of alcohol and the correct amount of water will not produce $Na_2SO_4$, if:
   (a) dissolved gases are present in appreciable quantities,
   (b) heavy anion and/or cation impurities are present in appreciable quantities, such as are often found in $ClO_2$ spent acids,
   (c) continuous addition of alcohol and high shear created by an agitator within the crystallizer — see FIG. 2 — are not practised.

Detailed descriptions regarding the foregoing are provided below.

It has been observed that, when the aforementioned organic compounds and, in particular, methanol are added to the highly acidic chlorine dioxide generator effluent, $Na_3H(SO_4)_2$ is precipitated. It has more importantly been observed that, when approximately 20% water by volume of the organic compound is simultaneously added, then the neutral sulfate is split out from the sesquisulfate and subsequently filtered. The rhombic crystals filter quickly and may be washed free of entrained mother liquor, using an aqueous solvent mixture or cold water alone.

The filtered sodium sulfate can be dried by heating and the entrained wash solvent recovered from the vapors by condensation. Alternatively, entrained solvent can be recovered with little loss by displacement washing of the sodium sulfate with cold water and the wet solid product returned to the kraft chemical recover system.

The organic compounds are all relatively volatile and thus can be recovered from the mother liquor by distillation. Water in the system prevents excessive methyl hydrogen sulfate formation in the time that the methanol and sulfuric acid are in contact. Furthermore, any methyl hydrogen sulfate that is formed has been found to be quickly reconverted back to free sulfuric acid and alcohol, during the removal of the methanol by distillation.

The sulfuric acid remains as still bottoms following the methanol distillation, and can be concentrated by water evaporation to the level required for reuse in the chlorine dioxide generator.

Laboratory experiments carried out on the present invention have illustrated that the separation process, according to the present invention, consists of three distinct stages. The mechanism of the present invention is believed to be that, upon addition of alcohol to the chlorine dioxide generators effluent, the following events occur in sequence:

STAGE 1: Precipitation of the acid salt monohydrate $NaHSO_4 \cdot H_2O$ occurs during the initial stages of alcohol addition.

STAGE 2: Upon further addition of alcohol, a rapid primary splitting of $NaHSO_4 \cdot H_2O$ into the intermediate acid salt $Na_3H(SO_4)_2$ occurs.

STAGE 3: Finally, when the alcohol addition dilutes the acid concentration to 4N or below, and provided water makes up 5 to 50% by volume of the alcohol, then a somewhat less rapid secondary splitting of the intermediate acid salt to $Na_2SO_4$ occurs.

The mechanism may be summarized as follows:

in effect. On the other hand, it has been observed that the following variances will affect the operation of the system:

| CONDITION 1: | |
|---|---|
| Feed Product: | 33% $H_2SO_4$ |
| | 24% $Na_2SO_4$ |
| | 43% $H_2O$ |
| Continuous Feed Product Rate: | 30 mls/min. |
| Continuous MeOH Feed to Crystallizer: | 70 mls/min. |
| Continuous $H_2O$ Feed to Crystallizer: | 11 mls/min. |
| RESULT: $Na_2SO_4$ produced. | |

CONDITION 2:

As Condition 1, but without degassification of feed product, i.e. dissolved $ClO_2$ and/or $Cl_2$ and/or $SO_2$.
RESULT: No $Na_2SO_4$, only $Na_3H(SO_4)_2$ made.

CONDITION 3:

As Condition 1 but containing 1 gpl of chromium $(Cr^{+++})$ from potassium dichromate in the sodium chlorate feed to the $ClO_2$ generator.
RESULT: No $Na_2SO_4$, only $Na_3H(SO_4)$ made.

CONDITION 4:

As Condition 1, but excess $NaClO_3$ residual remaining in $ClO_2$ generator spent acid.
RESULT: Approximately 50% $Na_2SO_4$ and $Na_3H(SO_4)_2$ made.

Figure 2:
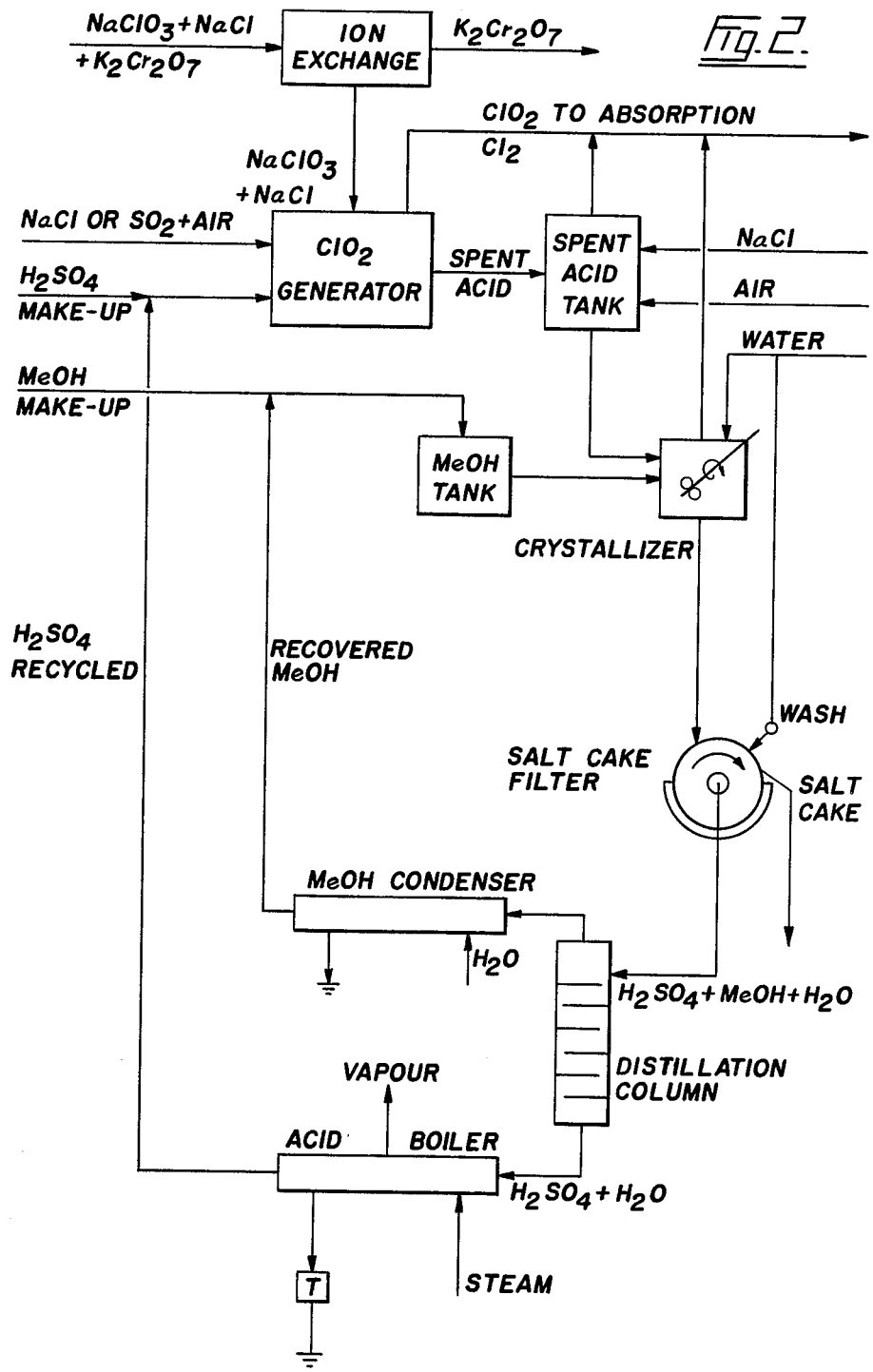
FIG. 2 is a flow diagram illustrating one embodiment of the process of the present invention.

Referring to FIG. 2, this illustrates a flow diagram of a typical process according to the invention. The process is as follows:

When potassium dichromate is contained in the sodium chlorate/salt solution the sodium chlorate - salt - water solution containing up to 3 grams per liter of potassium dichromate is fed to an ion exchange system where the dichromate is removed on the cationic resin. The sodium chlorate/salt water mixture containing up to 2 parts per million chromium ion is continuously fed to the chlorine dioxide generator. When the chlorate/salt solution is free of potassium dichromate sodium chlorate and water alone or a sodium chlorate/salt water solution are fed to the chlorine dioxide generator

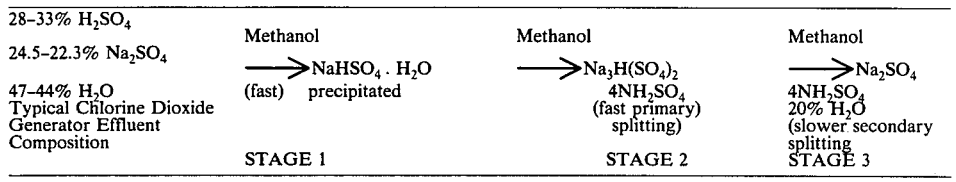

| 28–33% $H_2SO_4$ | | | |
|---|---|---|---|
| 24.5–22.3% $Na_2SO_4$ | Methanol | Methanol | Methanol |
| | $\longrightarrow NaHSO_4 \cdot H_2O$ | $\longrightarrow Na_3H(SO_4)_2$ | $\longrightarrow Na_2SO_4$ |
| 47–44% $H_2O$ | (fast) precipitated | 4$NH_2SO_4$ | 4$NH_2SO_4$ |
| Typical Chlorine Dioxide | | (fast primary) | 20% $H_2O$ |
| Generator Effluent | | splitting) | (slower secondary |
| Composition | | | splitting |
| | STAGE 1 | STAGE 2 | STAGE 3 |

A knowledge of the mechanism of the separation can be useful. For example, depending upon process conditions, the three stages can be observed separately or made to occur in rapid succession. Thus, the desired neutral sodium sulfate can be isolate directly with no evidence of the intermediate stages. On the other hand, depending upon the sulfidity requirements of the kraft mill, it may be desirable and more economical to separate the intermediate acid salt $Na_3H(SO_4)_2$ or only partially split this down to the neutral state by giving it a brief washing on the filter with fresh solvent. Experimental work has indicated that for best results the amount of organic compound added to the solution should at least the same as the spent generator acid volume. If the amount of organic compound is below this quantity the precipitation efficiency of the sodium sulfate from solution is seriously affected.

The separation process has been carried out at temperature in the range of 20° to 70° F, with little variation to be reduced either by sodium chloride, sulphur dioxide or methanol in a strong acid environment. The resulting chlorine dioxide or chlorine dioxide plus chlorine proceed to absorption in water and the bleaching process. In all cases, according to the invention, $ClO_2$ and $Cl_2$ gases are drawn from the generator while the spent acid containing between 25 and 35% $H_2SO_4$, 15 – 25% $Na_2SO_4$, the balance being unreacted $NaClO_3$, NaCl, dissolved $ClO_2$, $Cl_2$ and water, overflows to the Spent Acid Tank.

Salt (NaCl) and air are added to the spent acid where the residual sodium chlorate ($NaClO_3$) is reduced by the salt and the dissolved $ClO_2$ and $Cl_2$ gases are purged out by the air.

The degassed spent acid is then pumped to the crystallizer wherein methanol ($CH_3OH$) and water are added. Since there is a further, although remote, possibility of chlorine dioxide generation after the introduction of methanol, the crystallizer is vented to the $ClO_2$ gas line between the generator and absorption tower. After a retention of approximately 10 minutes, neutral sodium sulfate crystals are formed and the mixture of sodium sulfate, methanol, sulfuric acid and water is fed to a drum filter or other dewatering device.

The salt cake filter isolates the rhombic crystalline sodium sulfate from the acid-methanol-water mixture. After washing the crystal, the salt cake is discharged at approximately 90% w/w solids, the wet component consisting of traces of acidmethanol in mostly water.

Acid-methanol and water are pumped to a distillation column where the methanol is stilled off, condensed and returned to the methanol storage tank.

Still bottoms from the distillation column, consisting essentially of acid and water, overflow to an acid boiler where water is boiled off and the reconcentrated acid recycled back to the $ClO_2$ generator acid feed line. Fresh acid is introduced at this point to make up for possible cyclic losses.

The invention is illustrated in the following examples:

EXAMPLE 1

Precipitation of Sodium Bisulfate Monohydrate ($NaHSO_4 \cdot H_2O$) from R-2 Process Spent Acid Using Methanol One hundred grams (or 66 ml) of R-2 Process spent acid (23.5% $Na_2SO_4$, 33.2% $H_2SO_4$, 0.03% $Cr^{+++}$ ion and the balance water) was treated at approximately 30° C with 24 ml of methanol over a period of 3 minutes with stirring. The precipitated salt was separated by vacuum filtration and then pressed to give a cake whose air-dry solids content was 84%. The pale green product was air-dried. Yield 32.3 g. This material was found to contain 31.8% $H_2SO_4$ by titration with sodium hydroxide. (Pure $NaHSO_4 \cdot H_2O$ requires 35.5% $H_2SO_4$). The isolated product melted upon further drying in an oven set at 105° C and then resolidified. (Pure $NaHSO_4 \cdot H_2O$) is reported to melt at 58.5° C, at which temperature it loses its water of crystallization and is converted into solid anhydrous $NaHSO_4$ melting point 315° C.)

EXAMPLE 2

Isolation of Trisodium Hydrogen Disulfate ($Na_3H(SO_4)_2$) from Mathieson Process Spent Acid Using a Two-Stage Addition of Methanol One hundred grams of Mathieson Process spent acid (22.1% $Na_2SO_4$, 30.9% $H_2SO_4$ and the balance water) was treated at 30° C over a period of 3 minutes with 75 ml of methanol, whilst being stirred. The precipitated salt was separated using a vaccum filter and then pressed. Following this treatment, any entrained mother liquor was rapidly removed by pulling through the filter cake 20 ml of a mixture comprised of 80 parts by volume methanol and 20 parts by volume water (80% v/v methanol:water). The white product was then dried in an oven at 105° C. Yield 27.4 g, $H_2SO_4 = 17.5\%$, [$Na_3H(SO_4)_2$ requires 18.7% $H_2SO_4$].

EXAMPLE 3

Isolation of Essentially Pure Neutral Sodium Sulfate ($Na_2SO_4$) From Mathieson Process Spent Acid Using a Two-Stage Addition of Methanol One hundred grams of the same Mathieson Process spent acid described in Example 2 was treated at 30° C over a period of 3 minutes with 75 ml of methanol, whilst being stirred. The precipitated salt was then separated using a vacuum filter and pressed. Following this treatment, the filter cake was reslurried using 100 ml of 80% v/v methanol:water and allowed to stand for approximately 2 minutes, after which the solvent mixture was pulled through and the white product dried in an oven at 105° C.

Yield 23.1 g, $H_2SO_4 = 3.6\%$.

EXAMPLE 4

Isolation of Essentially Pure Neutral Sodium Sulfate ($Na_2SO_4$) From Mathieson Process Spent Acid Using One-Stage Addition of Methanol to the Spent Acid One hundred grams of the same Mathieson Process spent acid described in Example 2 was diluted with 41 ml of water prior to being treated at 30° C over 30 seconds with 244 ml of methanol. The mixture was stirred during the addition. After a further 4 minutes the slurry was separated on a vaccum filter and pressed. Following this treatment, any entrained mother liquor was rapidly removed by pulling through the filter cake 10 ml of 80% v/v methanol:water. The white product was then oven-dried at 105° C. Yield 21.9 g, $H_2SO_4 = 0.98\%$.

EXAMPLE 5

Isolation of Essentially Pure Neutral Sodium Sulfate ($Na_2SO_4$) From Mathieson Process Spent Acid Using One-Stage Addition of the Spent Acid to Methanol This example resembles Example 4 in regard to the quantities of material used and contact times, and differs from it only in that the spent acid was added to the methanol. Yield 21.2 g, $H_2SO_4 = 0.74\%$.

EXAMPLE 6

Isolation of Essentially Pure Neutral Sodium Sulfate ($Na_2SO_4$) Mathieson Process Spent Acid Using a Two-Stage Addition of Enthanol One hundred grams of Mathieson Process spent acid ($Na_2SO_4$ 24.5%, $H_2SO_4$ 28.6% and the balance water) was treated over a period of 10 seconds with 75 ml of ethanol at 30° C. The mixture was stirred during the addition. The precipitated salt was separated using a vacuum filter and pressed. The filter cake was reslurried with 100 ml of 80% v/v ethanol:water and allowed to stand for 2 minutes before the solvent was pulled through the filter cake. After drying, the product weighed 20.4 g, $H_2SO_4 = 1.9\%$.

EXAMPLE 7

Isolation of Trisodium Hydrogen Disulfate ($Na_3H(SO_4)_2$) From Mathieson Process Spent Acid Using Iso-Propanol One hundred grams of Mathieson Process spent acid, whose composition was described in Example 2, was treated over a period of 10 seconds with 40 ml of iso-propanol at 30° C. The mixture was stirred during the addition. The precipitated salt was separated using a vacuum filter and pressed. Following this treatment, any entrained mother liquor was rapidly removed by pulling through 10 ml of 80% v/v iso-propanol:water. The product was then dried in an oven at 105° C. Yield 22.7 g, $H_2SO_4 = 17.9\%$.

EXAMPLE 8

Recovery of Sulfuric Acid and Methanol from Mixtures in Water

A mixture composed of $H_2SO_4$ (670.4mE), water 33 g and methanol 75 ml (59.7 g), typical of a mother liquor isolated following separation of $Na_2SO_4$ was distilled at atmospheric pressure over a period of 40 minutes. The fraction collected between 63° and 98° C amounted to 85.13 g, whose specific gravity was 0.875, corresponding to 70% methanol, 30% water by weight; the recovery of pure methanol is therefore close to the theoretical amount. The pot residue weighed 49.9 g and had a specific gravity of 1.55, corresponding to 65% w/w $H_2SO_4$, or 32.4 g. The amount of $H_2SO_4$ recovered in the pot residue was also independently found to be 674 mE or 33.03 g by titration with alkali. This indicates that close to the theoretical amount of $H_2SO_4$ can be recovered from the original mixture.

EXAMPLE 9

Effect of Trivalent Chromium on Secondary Splitting of Tri-Sodium Hydrogen Disulfate ($Na_3H(SO_4)_2$)

One hundred grams of the same R-2 Process spent acid as used in Example I was treated with 75 ml of methanol at approximately 30° C within a period of 5 seconds. The stirred slurry mixture was then separated on a vacuum filter and the pressed filter cake reslurried for a period of 3 minutes with 100 ml of a mixture composed of 80 ml methanol and 20 ml water (80% v/v methanol:water). Following removal of the wash solvent, the product was dried in the oven at 105° C. Yield = 24.8 g of very pale green product, $H_2SO_4$ = 18.2%. [$Na_3(SO_4)_2$ requires 18.7% $H_2SO_4$.] Under similar conditions as given in Example 3, spent acid from the Mathieson Process (containing no trivalent chromium ion) resulted in neutral $Na_2SO_4$. The chromium therefore inhibits the secondary splitting reaction normally occurring in the reslurrying operation.

EXAMPLE 10

Continuous Isolation of Essentially Neutral Sodium Sulfate ($Na_2SO_4$) From Mathieson Process Spent Acid Using One-Stage Addition Mathieson Process spent acid, described in Example 2, was metered at 30 ml/min. into a stirred reaction vessel whose volume up to an overflow exit pipe was approximately 1800 ml. At the same time, methanol and water were also metered separately into the vessel at 70 ml/minutes and 8.5 ml/minutes, respectively. After approximately 10 minutes a slurry was collected from the overflow pipe and filtered continuously on a small vacuum drum filter, whose face, diameter and rotation speed were 7.5 cm, 12 cm and 1 rpm, respectively. Following removal of the mother liquor, the white solid product was washed on the drum and separated from entrained solvent and free sulfuric acid using approximately 10 ml/minutes of cold water. The product at 85% solids was removed continuously using a doctor blade, dried and found to contain less than 1% $H_2SO_4$ and less than 1% methanol. The clear mother liquor was found to contain 1.3% solids (as $Na_2SO_4$), which could be related back to an 86% precipitation efficiency of $Na_2SO_4$ from the original spent acid.

EXAMPLE 11

Continuous Isolation of a Mixture of Trisodium Hydrogen Disulfate and Neutral Sodium Sulfate Using One-Stage Addition Partially Split Salt)

Mathieson Process spent acid described in Example 2 was metered at 30 ml/minutes into the same stirred reaction vessel as mentioned in Example 10. Methanol 50 ml/minutes and water at 85 ml/minutes were also introduced into the vessel at the same time. After approximately 12 minutes the product was collected from the overflow pipe in the manner described in Example 10. After drying, the salt was found to contain 8.25% $H_2SO_4$. The clear mother liquor contained 2.25% solids (as $Na_2SO_4$), which relates back to an 80% precipitation efficiency of $Na_2SO_4$ from the original spent acid.

EXAMPLE 12

Isolation of a Mixture of Trisodium Hydrogen Disulfate and Neutral Sodium Sulfate Using a Two-Stage Addition of Acetone One hundred grams of the same Mathieson Process spent acid described in Example 2 was diluted with 41 ml of water prior to being treated with 244 ml of acetone over 30 seconds at 30° C with good agitation. After 12 min. the product was separated on a vacuum filter and pressed. A small sample of the solid product was removed from the cake at this stage, dried and found to contain 20.97% $H_2SO_4$, indicating that only primary splitting had so far been achieved. The remainder of the cake was slurried using 100 ml of 80% v/v acetone:water and allowed to stand for 5 minutes before the solvent was pulled through the filter cake. After drying, the product was found to contain 12.6% $H_2SO_4$. This indicated that secondary splitting of the neutral salt had been partially achieved during treatment with 80% v/v acetone:water over a period of 5 minutes.

We claim:

1. A method of separating sulfuric acid and anhydrous sodium sulfate from the effluent of a chlorine dioxide generator said effluent containing sulfuric acid, sodium sulfate, water, dissolved gases and multivalent cations, the method comprising:
   removing the multivalent cations from the effluent;
   oxidizing the residual chlorate in the effluent to chlorine dioxide and venting the chlorine dioxide;
   purging dissolved gases from the effluent;
   subjecting the purged effluent to high shear agitation while continually adding a mixture of an organic compound selected from alcohols and ketones with 5% to 50% water by volume, based on the volume of the organic compound, to adjust the normality of the effluent with respect to sulfuric acid to at most 4 and to precipitate anhydrous sodium sulfate from the effluent;
   passing the mother liquor from the sulfate separation to a distillation column;
   separating the organic compound from the distillate; and
   recovering sulfuric acid from the still bottoms.

2. A method as claimed in claim 1 in which the organic compound is methanol.

3. A method as claimed in claim 1 in which the multivalent cations are removed by passing the effluent through an ion exchange column.

4. A method as claimed in claim 1 in which the sulfate is formed in a crystallizer having an agitator.

5. A method as claimed in claim 1 in which the composition of the effluent is in the range 20 to 30% sulfate, 25 to 35% sulfuric acid, the balance being water plus impurities, the percentages being by weight.

* * * * *